United States Patent [19]

Alburger

[11] 4,089,213

[45] May 16, 1978

[54] NONSURFACTANT REMOVER COMPOSITION FOR INSPECTION PENETRANTS

[76] Inventor: James R. Alburger, 5007 Hillard Ave., La Canada, Calif. 91011

[21] Appl. No.: 813,618

[22] Filed: Jul. 7, 1977

[51] Int. Cl.² .................... G01N 21/16; C09K 11/06; C09K 3/00
[52] U.S. Cl. ................................. 73/104; 252/301.19; 252/408
[58] Field of Search ........................ 252/301.2 P, 408; 73/104

[56] References Cited

U.S. PATENT DOCUMENTS

| | | | |
|---|---|---|---|
| 3,561,262 | 2/1971 | Borucki | 73/104 |
| 3,607,333 | 9/1971 | Alburger | 73/104 |
| 3,642,655 | 2/1972 | Borucki | 73/104 |
| 3,715,227 | 2/1973 | Alburger | 252/301.2 P |
| 3,770,957 | 11/1973 | Alburger | 73/104 |
| 3,896,664 | 7/1975 | Alburger | 252/408 |
| 3,931,733 | 1/1976 | Alburger | 73/104 |
| 3,935,731 | 2/1976 | Alburger | 73/104 |
| 3,978,717 | 9/1976 | Alburger | 252/408 |
| 3,992,319 | 11/1976 | Alburger | 73/104 |

*Primary Examiner*—Benjamin R. Padgett
*Assistant Examiner*—T. S. Gron

[57] ABSTRACT

An improved inspection penetrant process employing a dyed liquid nonsurfactant-type penetrant, a remover, and a water rinse, in which the remover consists of a water solution of a nonsurfactant-type solvency accelerator which is selected from the group consisting of dihydroxybenzenes, carbamide and sodium benzoate. The penetrant, which is normally only slightly soluble in water, dissolves more readily in the solvency-accelerated water mixture, with the result that an improved removal of background porosity entrapments of penetrant is obtained, while entrapments of penetrant in crack defects are retained to a high level of entrapment efficiency.

5 Claims, No Drawings

NONSURFACTANT REMOVER COMPOSITION FOR INSPECTION PENETRANTS

RELATED PATENTS AND PATENT APPLICATIONS

U.S. Pat No. 3,896,664 for ENHANCED STABILITY WATER WASHABLE PENETRANT COMPOSITION AND PROCESS.

U.S. Pat No. 3,715,227 for INSPECTION PENETRANT DEVELOPMENT PROCESS EMPLOYING FUSIBLE WAXES.

Appln. Ser. No. 813,617, filed July 7, 1977 for METHOD OF RECYCLING NONSURFACTANT-TYPE REMOVERS IN INSPECTION PENETRANT PROCESSES.

This invention relates to inspection penetrant processes. More particularly, the invention relates to an improved remover composition which may be employed in inspection penetrant processes.

There are numerous modes of penetrant usage, but these are generally divided into three categories; e.g. water-washable processes, post-emulsifier processes, and solvent-remover processes. These processes differ from one another in the chemical nature of their various constituents, but they all operate in much the same way. In every case, parts to be tested for the presence of potential failure flaws are treated with a dyed liquid penetrant which enters into any surface cracks which may be present, forming entrapments therein. A remover is then applied, so as to remove excess surface penetrant and unwanted porosity background indications, and in some cases a finish water-rinse is employed. Finally, the test parts are dried, developed, and inspected for the presence of crack indications.

An important mode of penetrant usage is the so-called solvent-remover process. this process, or a variant mode known as the inhibited solvent-remover process, utilizes an oily water-insoluble penetrant, where the penetrant may contain either a visible-color dye, a fluorescent indicator dye, or both. Penetrant-treated test parts are processed in a remover which consists of a solvent liquid, as for example alcohol, so as to flush away excess surface penetrant and background entrapments of penetrant. Sometimes, the test parts are rinsed in plain water prior to drying, developing, and inspecting for flaw indications.

In the above-mentioned variant mode, the inhibited solvent-remover process, the remover solvent liquid may be an alcohol, a glycol, or a glycol-ether, and this solvent is diluted with water so as to reduce or inhibit the solvent strength of the remover. Inhibited-solvency removers may therefore be thought of as solvent removers which are slowed in their solvent action by dilution with water. They may also be thought of as water which is accelerated in its solvent action by the addition of a solvent coupler which tends to couple the normally water-insoluble oily penetrant into water solution.

The conventional solvent-coupler materials which are used in the inhibited-solvency mode of penetrant usage are liquid materials which act to dissolve background porosity entrapments of penetrant as well as entrapments of penetrant in actual cracks. The result is that under normal circumstances, in using such removers, indications of flaws may be greatly diminished or even lost completely during the remover contact time necessary for an adequate removal of background indications.

I have found that it is possible to formulate a new and unique type of inhibited-solvency remover, or more correctly an accelerated water remover, such that background porosity indications may be completely and cleanly removed from test surfaces without an excessive loss of actual crack indications.

The principal object of the invention, therefore, is to provide a new and novel remover composition which yields improved results in the detection of crack defects by the inspection penetrant process.

Other and incidental objects of the invention will in part be obvious and will in part become apparent from the following specification.

I have discovered that certain substances, which are not considered to be solvent materials at all, may be very effective as solvency accelerators for various kinds of low-solubility inspection penetrants, when the solvency accelerator is dissolved in water to make a solvent-remover composition. I have found at least five chemical materials which act as solvency accelerators for water, these substances being the following;

Hydroquinone,
Pyrocatechol,
Resorcinol,
Sodium benzoate, and
Carbamide,

The effect of solubility acceleration is particularly noticable when the accelerator substance is present in solution at the saturation point, however a useful acceleration of solubility may be obtained at concentrations as low as about five percent of saturation. The maximum concentrations which are obtainable with the above-identified accelerator materials may range from about 7 grams in 100 ml. water for hydroquinone, to 43.5 grams in 100 ml. water for pyrocatechol, to 62.5 grams per 100 ml. water for sodium benzoate, to 100 grams in 100 ml. water for carbamide (otherwise known as urea), to 500 grams in 100 ml. water for resorcinol. The solubility at saturation depends of course to some extent on the temperature of the water solution. It will be understood, therefore, that the solvency accelerator materials of the invention may be employed at concentrations ranging from saturation down to as low as about 0.35 percent, and will produce a significant degree of solvency acceleration, sufficient for the purpose of the invention.

In use, a water solution of an accelerator material of the invention is applied to penetrant-treated test parts in the same manner as an ordinary solvent remover or inhibited-solvency remover. A preferred method of operation is to first apply an oily water-insoluble or low-solubility inspection penetrant to parts being tested for the presence of surface flaws. The test parts are then surface-conditioned by treating all surfaces with a strong spray of water, whereby most of the thick-film residues of penetrant liquid are stripped off and drained back into the penetrant reservoir, being recovered by flotation.

The thus-conditioned test parts are then dipped in a water-solution of solubility accelerator for a time sufficient to yield an adequate removal of unwanted excess surface penetrant and porosity background entrapments. Alternatively, the remover composition of the invention may be applied to test surfaces by brush, wipe, or spray. The remover contact time may vary from a few seconds for a saturated solution of a solubility accelerator of the invention, up to several minutes for low-concentration solutions. In practice, the contact time which is utilized may be determined by the extent to which background indications must be depressed or removed. Also, the solvency effect of the accelerator mixtures of the invention may be influenced to a considerable degree by the amount of mechanical agitation of the remover solution against test surfaces, and by the temperature of the solution.

Finally, to complete the process, the test parts are rinsed in plain water for a few seconds, so as to flush off excess accelerator material, leaving a clean test surface. The test parts are then dried, developed, and inspected in the conventional manner.

As indicated above, the solvency-augmentating action of the accelerator materials of the invention is influenced by the temperature of the accelerator-water solutions. The preferred operating temperature is about 100° to 110° F., however room temperatures may be employed or the temperature may be as high as 130° F., or more. The temperature range of 100° to 110° F. is preferred for the reason that such temperatures are easy to control and maintain constant. Also, such temperatures do not create any severe problems of discomfort for workers who dip their hands into the working mixtures, or who work in processing rooms where the warm remover solutions are being sprayed onto test surfaces. In addition, an elevated temperature of the remover (and final rinse) acts to raise the temperature of test parts being processed, with the result that test surfaces may be readily dried after completion of the finish-rinse step, simply by blowing off excess surface water.

I have found that all of the known inspection penetrant compositions which are normally considered to be insoluble in water are actually slightly soluble, even though such solubility may be extremely small, considerably less than 0.001%. The solvency-accelerators of the invention are effective on any of such compositions, at least to the extent that the rate of penetrant removal from test surfaces is speeded up. For certain penetrant compositions where the solubility in water is extremely small, as in the case of a penetrant formulated using an aromatic mineral oil as a vehicle, the rate of removal of surface penetrant by use of a remover composition of the invention may be such that a remover contact time of 5 or 6 minutes at 100° F. is required. Plain water does not provide a useful removal of surface penetrant in cases of this kind.

A preferred category of inspection penetrant compositions for use with the remover compositions of the invention is that which is known commercially as "slow-solvbility" penetrants. These include materials which are described and claimed in my now-issued U.S. Pat No. 3,896,664. Penetrant compositions of this kind have water-solubilities which fall in the range of about 0.01% up to about 3%, and they are particularly advantageous in that they respond exceptionally well to the solvency-accelerator remover compositions of the invention.

The only restriction I make on the type of penetrant composition which is utilized for the purpose of the invention is that it must be non-surfactant in character. By this it is meant that the penetrant shall contain no detergent constituents which might produce emulsification upon contact with water. This is partly because the presence of a surfactant ingredient would tend to interfere with clarification and re-cycling of the remover by use of the solvent-extraction process which is described and claimed in my above-identified co-pending appln. Ser. No. 813,617. Most important is the fact that nonsurfactant-type penetrants yield much superior flaw detection results, as compared with other types, when used with the remover compositions of the invention.

The remover compositions of the invention yield quite unexpected and remarkable results in connection with the removal of unwanted background porosity entrapments of penetrant from porous test surfaces. I have found that if a saturated solution of carbamide or sodium benzoate, for example, is used with a slow-solubility-type penetrant based on a low-solubility polyoxyalkylene glycol or a low-solubility mono or diether of a polyoxyalkylene glycol, as is set forth in my above-mentioned U.S. Pat No. 3,896,664, as a vehicle, background porosity entrapments are removed cleanly from highly porous surfaces such as heat-resistant coatings on jet engine turbine blades, when a remover contact time of 30 seconds is employed, and with a remover temperature of 100° F. At the same time, indications of microflaws such as shallow craze-cracking are retained to a high level of flaw-entrapment efficiency. In contrast, when plain water (at 100° F.) is used as the remover, a remover contact time of 6 minutes must be employed, and even then a considerable amount of undesirable background indications remains.

Another quite remarkable result which is obtainable through use of the remover compositions of the invention is that entrapments in actual crack defects are preserved to such a high level of efficiency that no supplemental developer material is required. I have found that for most crack configurations, such as shallow craze cracks, stress cracks, or intercrystalline corrosion cracks, penetrant entrapments will "self-develop" by migrating out of such cracks to form minute exudations at or around the crack openings. Such self-development usually takes place within about 3 minutes to 10 minutes following the final rinse and drying of test parts. I have found that such "self-developed" indications of crack defects are considerably sharper and more well defined than are flaw indications which are developed in the conventional manner by use of a powder-type or nonaqueous powder suspension-type developer.

It should be mentioned that sodium benzoate, in water solution, has been utilized in the past as a "developer" in certain inspection penetrant processes, as for example in accordance with the teachings of my above-identified U.S. Pat. No. 3,715,227. For such usage, test parts which have been dipped in a penetrant, treated with a remover, and rinsed, are dipped in a solution of of sodium benzoate and a soluble wax, drained and immediately dried. As the liquid coating of developer solution dries on a test surface, an amorphous coating of solid particles of sodium benzoate precipitates onto the test surface, along with the soluble wax and other ingredients, and this coating of sodium benzoate acts as an assist for development, in the nature of a powder-type developer, such that entrapments of penetrant tend to migrate out of crack defects and become fixed on the sodium benzoate particles by capillary attraction. Such past usage of water solutions of sodium benzoate has been limited to developer applications, and the substance has never been suggested for use in remover compositions. Likewise, it will be understood that water solutions of dihydroxybenzenes and carbamide (urea) have never been utilized in the past, or suggested for use, as remover compositions.

Two of the solvency-accelerator materials of the invention, namely hydroquinone and pyrocatechol, tend to oxidize in air to form quinones, particularly if the water solution is slightly alkaline. Oxidation effects of this kind may be minimized or inhibited by including in the water solution a small amount of sodium sulfite, in accordance with known practices in photographic chemistry. It appears that water solutions of the materials; resorcinol, sodium benzoate, and carbamide, are quite stable, at least to the extent that they show no tendency to degrade, oxidize, or decompose for long periods of usage. All of the remover compositions of the invention are readily adaptable to clarification and recycling in accordance with the teachings of my above-identified appln, Ser. No. 813,617.

The derivation of a solubility-accelerated remover composition is not merely a matter of selecting a readily-soluble organic compound and dissolving it in water. For example, hexamethylene tetramine is soluble in water to the extent of about 67 grams in 100 ml. water. However, water solutions of this substance exhibit to evidence of solubility acceleration, that is for the purpose of this invention. I have theorized that other solubility-accelerator materials might be found, other than those which I have identified, such materials being compounds which have a carbon nucleus, a benzene nucleus, or a naphthalene nucleus, along with appropriate substituent groups which may impart water solubility. Thus, it is entirely possible that various chemical substances may be found, other than those listed above, which will provide solubility-accelerator results, that is for the purpose of the invention.

In cases where it is desired to maintain a saturated solution in water of a solubility-accelerator material of the invention, this may be readily accomplished simply by adding a sufficient amount of the solubility accelerator to a given volume of water so that no more accelerator material will dissolve. It will be understood, therefore, that saturated solutions, as utilized for the purpose of the invention, are water solutions containing concentrations of solubility-accelerator material which are at or near the maximum concentrations possible, at the working temperature of the solution.

Lower concentrations may be readily prepared and controlled to desired values by use of a hydrometer, where the specific gravity of the solvency-accelerator solution is adjusted to a specified value, as determined by a specific gravity/concentration calibration curve. Where the concentration of the solvency-accelerator solution is relatively low, in the range of 10% or less, it may be feasible and practical to omit the finish-rinse step of the process. Test parts which have been processed through the remover solution of the invention may be withdrawn from the remover solution, drained, and allowed to dry. With such low concentrations of accelerator solids, the amount of dry residue material left on test surfaces may be so small that it will be virtually invisible, and will not interfere with subsequent development and inspection for flaw indications. It will be understood, therefore, that the finish-rinse step of the process of the invention is optional, and may be omitted under appropriate circumstances.

It will be understood that the remover contact time which is utilized in the process of the invention may vary considerably depending on the nature of the base vehicle of the penetrant material which is employed. Although I make no restrictions on the chemical composition of the penetrant, I prefer to use a penetrant composition in combination with a remover composition of the invention such that remover contact times in the range of about 30 seconds up to about 3 minutes will yield adequate removal of background porosity entrapments.

If test parts are being processed by hand, where an operator manually dips parts or baskets of parts into the processing solutions, it is usually desirable to employ a short remover contact time, in the range of 30 seconds, so that test parts may be quickly moved through the process steps. On the other hand, where automated equipment is utilized for handling large test objects, such as jet engine turbine wheels or shrouds, or where large surfaces such as aircraft wing panels must be processed, it is usually more desirable to employ a remover contact time of about 3 minutes or more, so as to allow sufficient time to transport the test parts through the process step.

The process of the invention is adaptable to various requirements of remover contact time, by selection of an appropriate penetrant formulation, and by selection of an appropriate concentration of a solvency accelerator material of the invention. For most industrial requirements of nondestructive testing by the inspection penetrant process, highly satisfactory flaw-detection results may be obtained by using either one of two preferred penetrant compositions consisting of low-solubility base vehicles of (a) a polyoxyethylene glycol material, or (b) 2,2,4-trimethyl-1,3-pentanediol-diisobutyrate, wherein the penetrant vehicle contains fluorescent indicator dyes appropriate to provide a level of dye-performance sensitivity commonly known in the industry as "Tracer-Tech Level 7" . Either one of these two preferred penetrants, or similar materials, may then be employed with either one of two preferred remover compositions of the invention, such as (c) as saturated solution of urea or (d) a saturated solution of sodium benzoate. In all cases, the preferred operating temperature of the process materials is about 100° F., and the practical remover contact time is in the range of 30 seconds to 3 minutes.

It will be seen from the foregoing specification that I have devised a new and novel remover composition for inspection penetrant usage. Although the invention has been described with reference to particular embodiments thereof, it will be understood that various changes may be made therein without departing from the spirit of the invention of the scope of the appended claims.

I claim:

1. In an inspection penetrant process employing a dyed liquid nonsurfactant-type penetrant, a remover, and an optional finish water-rinse, wherein parts to be tested for the presence of surface flaws are first treated with said penetrant, excess surface penetrant is removed in a surface-conditioning step, background porosity entrapments are removed by washing said test parts in said remover, and said test parts are dried, developed, and inspected for the presence of flaw indications, the improvement in which said remover consists of a water solution of a solvency accelerator, said solvency accelerator being at least one member selected from the group consisting of
Hydroquinone,
Pyrocatechol,
Resorcinol,
Sodium benzoate, and
Carbamide (urea).

2. A process in accordance with Claim 1, in which said remover consists of a saturated solution of sodium benzoate.

3. A process in accordance with claim 1, in which said remover consists of a saturated solution of carbamide (urea).

4. A process in accordance with claim 1, in which said remover composition consists of a water solution of carbamide (urea) at a concentration within the range of from about 0.35% to about 50% by weight.

5. A process in accordance with claim 1 in which a supplemental step of finish-rinsing in water is added following the step of washing in said remover, and prior to said drying, developing, and inspecting said test parts.

* * * * *